(12) United States Patent
Gerbi et al.

(10) Patent No.: US 6,620,173 B2
(45) Date of Patent: Sep. 16, 2003

(54) METHOD FOR INTRODUCING AN END EFFECTOR TO A SURGICAL SITE IN MINIMALLY INVASIVE SURGERY

(75) Inventors: Craig Richard Gerbi, San Carlos, CA (US); Daniel T. Wallace, Redwood, CA (US)

(73) Assignee: Intuitive Surgical, Inc., Sunnyvale, CA (US)

(*) Notice: Subject to any disclaimer, the term of this patent is extended or adjusted under 35 U.S.C. 154(b) by 0 days.

(21) Appl. No.: 09/872,750

(22) Filed: May 31, 2001

(65) Prior Publication Data

US 2002/0045905 A1 Apr. 18, 2002

Related U.S. Application Data

(60) Provisional application No. 60/111,713, filed on Dec. 8, 1998, and provisional application No. 60/111,711, filed on Dec. 8, 1998.

(51) Int. Cl.[7] ............................................. A61B 19/00
(52) U.S. Cl. ...................................................... 606/130
(58) Field of Search .................... 606/1, 130; 600/203; 700/245, 258

(56) References Cited

U.S. PATENT DOCUMENTS

| | | |
|---|---|---|
| 4,843,939 A | 7/1980 | Hoover |
| 4,281,447 A | 8/1981 | Miller et al. |
| 4,332,066 A | 6/1982 | Hailey et al. |
| 4,486,928 A | 12/1984 | Tucker et al. |
| 4,500,065 A | 2/1985 | Hennekes et al. |
| 4,512,709 A | 4/1985 | Hennekes et al. |
| 4,706,372 A | 11/1987 | Ferrero et al. |
| 4,710,093 A | 12/1987 | Zimmer et al. |
| 4,793,053 A | 12/1988 | Zuccaro et al. |
| 4,809,747 A | 3/1989 | Choly et al. |
| 4,830,569 A | 5/1989 | Jannborg |
| 4,832,198 A | 5/1989 | Alikhan |
| 4,979,949 A | 12/1990 | Matsen, III et al. |
| 4,996,975 A | 3/1991 | Nakamura |
| 5,018,266 A | 5/1991 | Hutchinson et al. |

(List continued on next page.)

FOREIGN PATENT DOCUMENTS

| | | |
|---|---|---|
| WO | WO 93/13918 | 7/1993 |
| WO | WO 94/26167 | 11/1994 |
| WO | WO 96/16386 | 6/1995 |
| WO | WO 95/30964 | 11/1995 |
| WO | WO 96/38944 | 12/1998 |

OTHER PUBLICATIONS

Alexander, Aruthur D., "Impacts of Telemation on Modern Society," First CISM–IFToMM Symposium (Sep. 5–8, 1973) vol. II, pp. 122–136.

Alexander, Arthur D., "A survey Study of Teleoperators, Robotics, and Remote Systems Technology," California Institute of Technology (1973) pp. 448–458.

Alexander, Arthur D., "Endocorporeal Surgery Using Remote Manipulators," California Institute of Technology (1973) pp. 483–492.

*Primary Examiner*—Kevin Shaver
*Assistant Examiner*—Michael B. Priddy
(74) *Attorney, Agent, or Firm*—Townsend Townsend & Crew LLP; Mark D. Barrish, Esq.

(57) ABSTRACT

A tool guide for guiding an end effector of a robotically controlled surgical instrument from a position outside a patient body to a position in close proximity to an internal surgical site within the patient body is provided. The tool guide typically comprises a body, a seat formation on the body, the seat formation being arranged to seat in an aperture leading into the patient body so as to mount the tool guide on the patient body, and a sheath formation on the body. The sheath formation typically defines a longitudinally extending internal passage, an inlet leading into the passage and an outlet leading from the passage.

22 Claims, 10 Drawing Sheets

U.S. PATENT DOCUMENTS

| | | | |
|---|---|---|---|
| 5,078,140 A | 1/1992 | Kwoh | |
| 5,143,453 A | 9/1992 | Weynant nee Girones | |
| 5,154,717 A | 10/1992 | Matsen, III et al. | |
| 5,174,300 A | 12/1992 | Bales et al. | |
| 5,217,003 A * | 6/1993 | Wilk | 600/109 |
| 5,221,283 A | 6/1993 | Chang | |
| 5,236,432 A | 8/1993 | Matsen, III et al. | |
| 5,255,429 A | 10/1993 | Nishi et al. | |
| 5,257,998 A | 11/1993 | Ota et al. | |
| 5,271,384 A | 12/1993 | McEwen et al. | |
| 5,294,209 A | 3/1994 | Naka et al. | |
| 5,305,203 A * | 4/1994 | Raab | 606/1 |
| 5,312,212 A | 5/1994 | Naumec | |
| 5,313,935 A | 5/1994 | Kortenbach et al. | |
| 5,343,385 A | 8/1994 | Joskowicz et al. | |
| 5,354,314 A | 10/1994 | Hardy et al. | |
| 5,355,743 A | 10/1994 | Tesar | |
| 5,359,993 A | 11/1994 | Slater et al. | |
| 5,372,147 A | 12/1994 | Lathrop, Jr. et al. | |
| 5,397,323 A | 3/1995 | Taylor et al. | |
| 5,399,951 A | 3/1995 | Lavallee et al. | |
| 5,400,267 A | 3/1995 | Denen et al. | |
| 5,402,801 A | 4/1995 | Taylor | |
| 5,403,319 A | 4/1995 | Matsen, III et al. | |
| 5,417,210 A | 5/1995 | Funda et al. | |
| 5,427,097 A | 6/1995 | Depp | |
| 5,451,368 A | 9/1995 | Jacob | |
| 5,515,478 A | 5/1996 | Wang | |
| 5,634,937 A * | 6/1997 | Mollenauer et al. | 606/213 |
| 5,649,956 A | 7/1997 | Jensen et al. | |
| 5,657,429 A | 8/1997 | Wang et al. | |
| 5,697,939 A | 12/1997 | Kubota et al. | |
| 5,752,970 A * | 5/1998 | Yoon | 606/185 |
| 5,754,741 A | 5/1998 | Wang et al. | |
| 5,762,458 A | 6/1998 | Wang et al. | |
| 5,792,135 A | 8/1998 | Madhani et al. | |
| 5,800,423 A | 9/1998 | Jensen | |
| 5,815,640 A | 9/1998 | Wang et al. | |
| 5,855,583 A | 1/1999 | Wang et al. | |
| 5,878,193 A | 3/1999 | Wang et al. | |
| 5,907,664 A | 5/1999 | Wang et al. | |
| 5,971,976 A | 10/1999 | Wang et al. | |
| 6,132,368 A | 10/2000 | Cooper | |
| 6,459,926 B1 * | 10/2002 | Nowlin et al. | 600/429 |
| 2002/0133173 A1 * | 9/2002 | Brock et al. | 606/130 |

* cited by examiner

METHOD FOR INTRODUCING AN END EFFECTOR TO A SURGICAL SITE IN MINIMALLY INVASIVE SURGERY

CROSS-REFERENCES TO RELATED APPLICATIONS

This application is related to the following patents and patent applications, the full disclosures of which are incorporated herein by reference:

PCT International Application No. PCT/US98/19508, entitled "Robotic Apparatus", filed on Sep. 18, 1998, U.S. application Ser. No. 60/111,713, entitled "Surgical Robotic Tools, Data Architecture, and Use ", filed on Dec. 8, 1998, U.S. application Ser. No. 60/111,711, entitled "Image Shifting for a Telerobtic System", filed on Dec. 8, 1998;

U.S. application Ser. No. 09/378,173 , entitled "A Stereo Imaging System and Method for Use in Telerobotic Systems", filed on Aug. 20, 1999;

U.S. application Ser. No. 09/398,507 , entitled "Master Having Redundant Degrees of Freedom", filed on Sep. 17, 1999, U.S. application Ser. No. 09/399,457 , entitled "Dynamic Association of Master and Slave in a Minimally Invasive Telesurgery System", filed on Sep. 17, 1999;

U.S. application Ser. No. 09/373,678 , entitled "Camera Referenced Control in a Minimally Invasive Surgical Apparatus", filed on Aug. 13, 1999, now U.S. Pat. No. 6,424,885, U.S. application Ser. No. 09/398,598 entitled "Surgical Tools for Use in Minimally Invasive Telesurgical Applications", file on Sep. 17, 1999, now U.S. Pat. No. 6,394,998; and U.S. Pat. No. 5,808,665, entitled "Endoscopic Surgical Instrument and Method for Use", issued on Sep. 15, 1998.

BACKGROUND OF THE INVENTION

This invention generally relates to a tool guide for guiding an end effector of a robotically controlled surgical instrument from a position outside a patient body to a position within the patient body.

Minimally invasive medical techniques are aimed at reducing the amount of extraneous tissue which may be damaged during diagnostic or surgical procedures, thereby reducing patient recovery time, discomfort, and deleterious side effects. Many surgeries are performed each year in the United States. A significant amount of these surgeries potentially can be performed in a minimally invasive manner. However, only a relatively small percentage of surgeries currently use minimally invasive techniques due to limitations of minimally invasive surgical instruments and techniques currently used, and the difficulty experienced in performing surgeries using such traditional instruments and techniques.

Advances in minimally invasive surgical technology could dramatically increase the number of surgeries performed in a minimally invasive manner. The average length of a hospital stay for a standard surgery is significantly longer than the average length for the equivalent surgery performed in a minimally invasive surgical manner. Thus, expansion in the use of minimally invasive techniques could save millions of hospital days, and consequently millions of dollars annually, in hospital residency costs alone. Patient recovery times, patient discomfort, surgical side effects, and time away from work can also be reduced by expanding the use of minimally invasive surgery.

Traditional forms of minimally invasive surgery include endoscopy. One of the more common forms of endoscopy is laparoscopy, which is minimally invasive inspection or surgery within the abdominal cavity. In traditional laparoscopic surgery a patient's abdominal cavity is insufflated with gas and cannula sleeves are passed through small incisions in the musculature of the patient's abdomen to provide entry ports through which laparoscopic surgical instruments can be passed in a sealed fashion. Such incisions are typically about ½ inch (about 12 mm) in length.

The laparoscopic surgical instruments generally include a laparoscope for viewing the surgical field and working tools defining end effectors. Typical surgical end effectors include clamps, graspers, scissors, staplers, and needle holders, for example. The working tools are similar to those used in conventional (open) surgery, except that the working end or end effector of each tool is separated from its handle by a long extension tube, typically of about 12 inches (about 300 mm) in length, for example, so as to permit the surgeon to introduce the end effector to the surgical site and to control movement of the end effector relative to the surgical site from outside a patient's body.

To perform surgical procedures, the surgeon typically passes these working tools or instruments through the cannula sleeves to the internal surgical site and manipulates the instruments or tools from outside the abdomen by sliding them in and out through the cannula sleeves, rotating them in the cannula sleeves, levering (i.e., pivoting) the instruments against the abdominal wall and actuating the end effectors on distal ends of the instruments from outside the abdominal cavity. The instruments normally pivot around centers defined by the incisions which extend through the muscles of the abdominal wall. The surgeon typically monitors the procedure by means of a television monitor which displays an image of the surgical site captured by the laparoscopic camera. Typically, the laparoscopic camera is also introduced through the abdominal wall so as to capture the image of the surgical site. Similar endoscopic techniques are employed in, e.g., arthroscopy, retroperitoneoscopy, pelviscopy, nephroscopy, cystoscopy, cisternoscopy, sinoscopy, hysteroscopy, urethroscopy, and the like.

There are many disadvantages relating to such traditional minimally invasive surgical (MIS) techniques. For example, existing MIS instruments typically deny the surgeon the flexibility of tool placement found in open surgery. Difficulty is often experienced in approaching the surgical site with the instruments through the small incisions. The length and construction of many of the instruments reduces the surgeon's ability to feel forces exerted by tissues and organs on the end effectors. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of the tools has been found to be an impediment in the expansion of the use of minimally invasive surgery.

Minimally invasive telesurgical systems for use in surgery have been and are still being developed to increase a surgeon's dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the remote location whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

Typically, such a telesurgery system can be provided with at least two master control devices (one for each of the surgeon's hands), which are normally operatively associated with two robotic arms on each of which a surgical instrument is mounted. Operative communication between master control devices and associated robotic arm and instrument assemblies is typically achieved through a control system. The control system typically includes at least one processor which relays input commands from the master control devices to the associated robotic arm and instrument assemblies and from the arm and instrument assemblies to the associated master control devices in the case of, e.g., force feedback, or the like.

During the performance of a surgical procedure at an internal surgical site within a patient body using a minimally invasive telesurgical system as described above, it can happen that the surgeon desires replacing or exchanging one surgical instrument with another so as to introduce a specific desired end effector to the internal surgical site. This may be required when different surgical tasks, such as, for example, suturing, cauterization, excision, applying surgical clips, and the like, need to be performed during the same surgical procedure. Replacing, or exchanging, one surgical instrument with another can involve withdrawing the one surgical instrument from the patient body and introducing another surgical instrument to the surgical site. Such replacement typically includes introducing the end effector of the other surgical instrument to the surgical site by passing the end effector of the other surgical instrument through an aperture leading into the patient body and navigating the end effector from the aperture through part of the patient body so as to introduce it to the surgical site. Such replacement of surgical instruments may be desired several times during a surgical procedure.

It has been found that introducing the end effector to the surgical site in this manner, can be rather difficult. One reason for this, for example, is that a degree of care should be exercised so as to inhibit unnecessary injury to healthy tissue by the end effector as it is navigated through the part of the patient body. In consequence of the navigation difficulties, for example, the time taken to replace one surgical instrument with another can be uncomfortably long and the risk of unnecessarily injuring healthy tissue is ever present. It would be advantageous to provide a tool guide which enables a surgical instrument to be introduced to an internal surgical site without having to navigate it through the patient body to the internal surgical site.

To position the surgical instruments relative to a patient body at the commencement of a surgical procedure using a robotically controlled surgical system as described above, incisions are typically made where the instruments are to enter the patient body. Sometimes, the robotic arms of the surgical system are then maneuvered to position guides on the arms in the incisions. The guides on the robotic arms then serve to guide the surgical instruments through the incisions and into the patient body.

It has been found that maneuvering a robotic arm so as to position the guide thereon in the incision can be rather cumbersome and difficult. It would be advantageous to provide a device and/or method to ease the task of locating a robotic arm relative to an incision.

When performing a surgical procedure with such a robotic surgical system, it may be necessary to relocate one of the arms relative to the patient body so as to pass a surgical instrument on that robotic arm through another incision in the patient body. In such a case, it is often required to seal the incision from which the surgical instrument has been removed e.g., by means of suturing, or the like. This is especially true if the surgical procedure is performed in a patient's abdominal cavity, for example, and in which insufflation of the patient's abdominal cavity is required.

It has been found that such sealing operations during the course of a surgical procedure can unnecessarily complicate and prolong the surgical procedure. It would be advantageous if a robotic arm can selectively be associated with different apertures leading into a patient body without having to perform a suturing task, or the like, so as to seal the incision from which the instrument has been removed.

SUMMARY OF THE INVENTION

Accordingly, the invention relates to a device and method which can be employed so as to ease the task of introducing a robotically controlled surgical instrument to an internal surgical site.

In accordance with one aspect of the invention, there is provided a tool guide for guiding an end effector of a robotically controlled surgical instrument from a position outside a patient body to a position in close proximity to an internal surgical site within the patient body, the end effector typically being mounted at an end of a shaft of the surgical instrument. The tool guide comprises a tool guide body. A seat formation is provided on the tool guide body. The seat formation is arranged to seat in an aperture leading into the patient body so as to mount the tool guide on the patient body. Furthermore, a sheath formation is provided on the tool guide body. The sheath formation defines a passage, an inlet, or entry port, leading into the passage and an outlet, or exit port, leading from the passage. The sheath formation is arranged to cooperate with the seat formation such that when the seat formation is seated in the aperture, the outlet is positionable in close proximity to the surgical site, thereby to enable the end effector to be guided to a position in close proximity to the surgical site by passing it through the inlet, along the passage and out from the outlet so as to emerge from the outlet at the position in close proximity to the surgical site.

By providing such a tool guide, the surgical instrument is guided in the passage of the tool guide until it emerges at the surgical site. Accordingly, navigation of the surgical instrument through body tissue extending between the aperture leading into the patient body and the surgical site is made relatively easy since the tissue is protected by the tool guide. Accordingly, the surgical instrument can be introduced to the surgical site readily by simply passing it through the passage of the tool guide. The guide further comprises a seat formation for seating it in an aperture leading into the patient body. Accordingly, the tool guide can readily be mounted on a patient body by positioning the seat formation in the aperture so that the sheath formation extends to a position in close proximity to the surgical site.

In accordance with another aspect of the invention, there is provided a method of performing a surgical procedure. The method comprises locating a sheath formation in a mounted condition in an aperture leading into the patient body. The sheath formation typically defines a passage, an inlet leading into the passage and an outlet leading from the passage. The inlet is typically accessible from outside the patient body when the sheath formation is in the mounted condition. The method further comprises positioning the outlet in close proximity to a surgical site within the patient body and passing an end effector of a robotically controlled surgical instrument through the inlet, along the passage and out from the outlet so as to emerge from the outlet at a position in close proximity to the surgical site. The method further comprises robotically controlling the surgical instrument to cause the end effector to perform at least part of a surgical procedure at the surgical site.

In accordance with another aspect of the invention, there is provided a tool guide kit for use in guiding an end effector of a robotically controllable surgical instrument from a position outside a patient body to a position in close proximity to a surgical site within the patient body, the end effector being mounted at an end of a shaft of the surgical instrument. The tool guide kit comprises a plurality of tool guides, each tool guide comprising a tool guide body and a seat formation on the tool guide body. The seat formation is arranged to seat in an aperture leading into the patient body so as to mount the tool guide on the patient body. Each tool guide further comprises a sheath formation on the tool body, the sheath formation defining a passage, an inlet leading into the passage and an outlet leading from the passage. The sheath formation of tool guides have a variety of different lengths. The lengths spanning a select range of depths of surgical sites from the aperture in the body wall. Typically, the lengths fall in the range between about 25 mm and about 250 mm so that a tool guide having a sheath formation length corresponding to a distance between the aperture in the patient body and the surgical site can be selected from the tool guide kit so that when the selected tool guide is mounted on the patient body, its sheath formation can be positioned such that its outlet is in close proximity to the surgical site thereby to enable the end effector to be guided to a position in close proximity to the surgical site by passing it through the inlet, along the passage and out from the outlet, so as to emerge from the outlet at the position in close proximity to the surgical site.

The invention further relates to a device and method which can be employed so as to ease the task of locating a robotic arm relative to an aperture leading into a patient body so that a surgical instrument operatively associated with the arm can be passed through the aperture.

Accordingly, in accordance with another aspect of the invention, there is provided a method of performing a robotically controlled surgical procedure in which the method comprises mounting a tool guide in an aperture leading into a patient body. The tool guide defines a passage extending from an inlet of the tool guide to an outlet of the tool guide. The inlet is accessible from outside the patient body and the outlet is positioned within the patient body when the tool guide is mounted in the aperture. The method further comprises coupling the tool guide to a robotic arm while the tool guide is mounted in the aperture. The method still further comprises performing at least part of a surgical procedure with a robotically controlled surgical instrument operatively connected to the robotic arm and extending through the inlet, along the passage and out from the outlet of the tool guide.

In accordance with yet a further aspect of the invention, there is provided a tool guide. The tool guide comprises an elongated body defining opposed ends and a passage extending longitudinally along the body between the opposed ends. The tool guide further comprises an engaging formation on the body, the engaging formation being arranged to cooperate with a complementary engaging formation on a robotic arm, so that the tool guide can be mounted in an aperture leading into a patient body and the robotic arm can be coupled to the tool guide while the tool guide is mounted in the aperture.

By first locating such a tool guide in the aperture leading into the patient body and then coupling the robotic arm to the guide when mounted in the aperture, the task of locating the robotic arm relative to the aperture is at least alleviated when compared with inserting a guide on the arm into the aperture.

Another aspect of the invention includes a method of preparing for robotic surgery, which comprises determining one or more locations in a patient's body surface for the placement of incisions or "ports" for tool insertion during a robotic surgical procedure; cutting an incision at each port location; inserting a tool guide as described herein through the incision; and preferably sealing the tool guide with a sealing formation. The sealing formations prevent loss of insufflation gas, and closes the port/tool guide until it is needed. Subsequently, tools may be inserted into the pre-located tool guides to perform the surgical procedure. The method described permits pre-planing and arranging of port placement, optionally with additional tool guides to be pre-located, so that tools may be quickly exchanged between ports during surgery.

Note that, unless the context indicates otherwise, a reference to a surgical tool or instrument herein may include tools having a variety of surgical purposes, such as an endoscope; a tissue treatment tool, a diagnostic or imaging probe, a tissue retractor or stabilizer, an irrigation or suction tool, a combination function instrument, a surgical accessory, a surgical accessory support or container device, and the like.

BRIEF DESCRIPTION OF THE DRAWINGS

FIG. 7 shows, at an enlarged scale, a schematic sectional side view of the tool guide shown in FIG. 6;

FIG. 8 shows, at an enlarged scale, a schematic sectional side view of another tool guide in accordance with the invention;

DESCRIPTION OF THE SPECIFIC EMBODIMENTS

Figure 1:
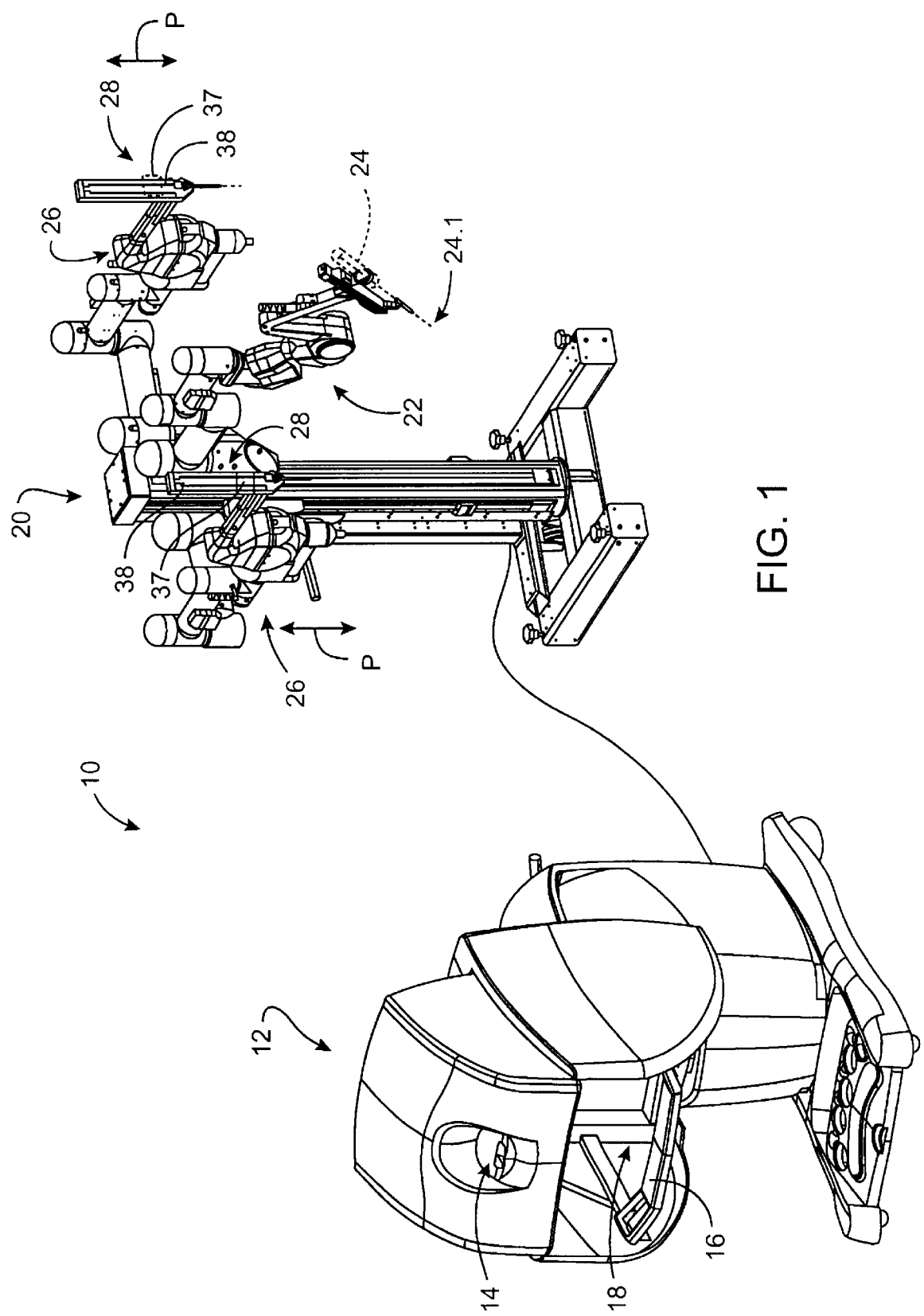
FIG. 1 shows a three-dimensional view of an operator control station, or surgeon's console, and a surgical work station, or cart, of a telesurgical system, the cart carrying three robotically controlled arms, the movement of the arms being remotely controllable from the control station.

Referring to FIG. 1 of the drawings, a minimally invasive telesurgical system, or robotically controlled surgical system, is generally indicated by reference numeral 10. The system 10 includes a control station, or surgeon's console, generally indicated by reference numeral 12. The station 12 includes an image display or viewer 14 where an image of a surgical site is displayed in use. A support 16 is provided on which an operator, typically a surgeon, can rest his or her forearms while gripping two master control devices, one in each hand. The master control devices are positioned in a space 18 inwardly beyond the support 16. When using the control station 12, the surgeon typically sits in a chair in front of the control station 12, positions his or her eyes in front of the viewer 14 and grips the master controls one in each hand while resting his or her forearms on the support 16.

The system 10 further includes a surgical work station, or cart, generally indicated by reference numeral 20. In use, the cart 20 is positioned in close proximity to a patient requiring surgery and is then normally caused to remain stationary until a surgical procedure to be performed by means of the system 10 has been completed. The cart 20 typically has wheels or castors to render it mobile. The station 12 is typically positioned remote from the cart 20 and can be separated from the cart 20 by a great distance, even miles away, but will typically be used within an operating room with the cart 20.

The cart 20 typically carries at least three robotic arms, or robotic arm assemblies. One of the robotic arm assemblies, indicated by reference numeral 22, is arranged to hold an image capture device 24, e.g., an endoscope, or the like. Each of the other two arm assemblies 26, 26 respectively, is arranged to hold a robotically controlled surgical instrument 28. An example of a typical surgical instrument 28 will be described in greater detail below and with reference to FIG. 2 of the drawings. The endoscope 24 has an object viewing end 24.1 at a remote end of an elongate shaft thereof. It will be appreciated that the endoscope 24 has an elongate shaft to permit its viewing end 24.1 to be inserted through an entry port or aperture in a patient's body so as to access an internal surgical site. The endoscope 24 is operatively connected to the viewer 14 to display an image captured at its viewing end 24.1 on a display area of the viewer 14. Each robotic arm assembly 26, 26 is normally operatively connected to one of the master controls. Thus, the movement of the robotic arm assemblies 26, 26 is controlled by manipulation of the master controls. The instruments 28, 28 on the robotic arm assemblies 26, 26 typically have end effectors which are mounted on wrist-like mechanisms which are pivotally mounted on distal ends of elongate shafts of the instruments 28, 28. It will be appreciated that the instruments 28, 28 have elongate shafts to permit the end effectors to be inserted through entry ports or apertures in a patient's body so as to access the internal surgical site. Movement of the end effectors relative to the ends of the shafts of the instruments 28, 28 is also controlled by the master controls. When a surgical procedure is to be performed, the cart 20 carrying the robotic arms 22, 26, 26 is wheeled to the patient and is normally maintained in a stationary position relative to, and in close proximity to, the patient, during the surgical procedure.

Figure 2:
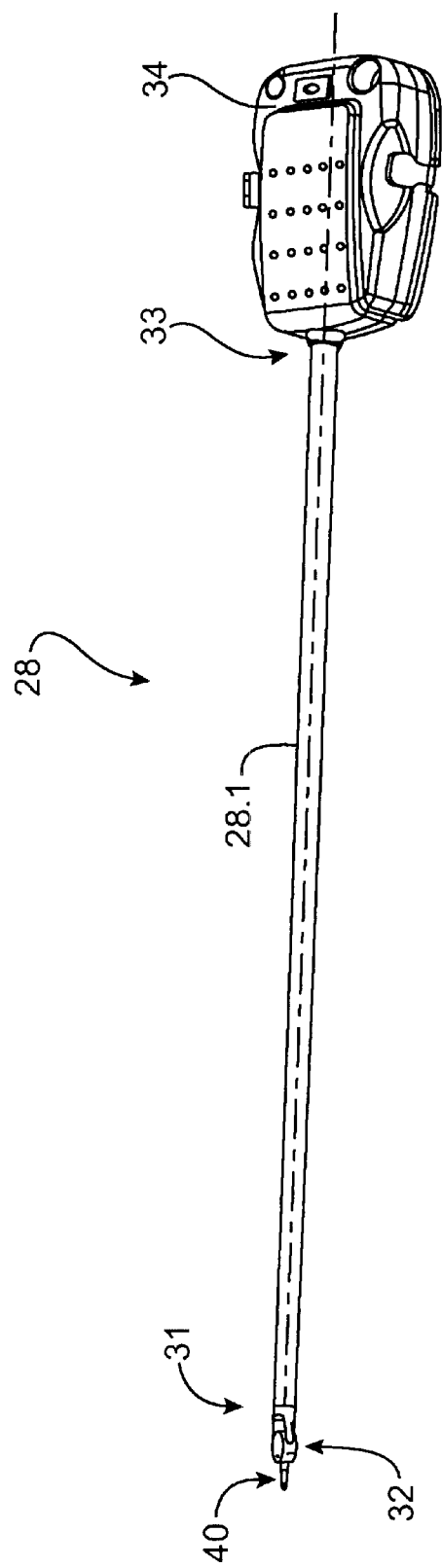
FIG. 2 shows, at an enlarged scale, a three-dimensional view of a typical surgical instrument used with the system shown in FIG. 1.

Referring to FIG. 2 of the drawings, a typical surgical instrument 28 will now be described in greater detail. The surgical instrument 28 includes an elongate shaft 28.1. The elongate shaft 28.1 defines opposed ends 31 and 33. The wrist-like mechanism, generally indicated by reference numeral 32, is located at the end 31 of the shaft 28.1. A housing 34, arranged releasably to couple the instrument 28 to one of the robotic arm assemblies 26, 26 is located at the other end 33 of the shaft 28.1. Referring again to FIG. 1 of the drawings, the instrument 28 is typically releasably mountable on a carriage 37 so as operatively to connect the instrument to the robotic arm 26. The carriage 37 can be driven to translate along a linear guide formation 38 of the arm 26 in the direction of arrows P.

As can best be seen in FIG. 2 of the drawings, at the end of the wrist-like mechanism 32, the surgical instrument 28 typically carries an end effector, generally indicated by reference numeral 40. The end effector 40 can be in the form of any one of a plurality of different end effectors. For example, the end effector 40 can be in the form of a jaw-like arrangement, such as, for example, forceps, a clip applier for anchoring surgical clips, scissors, needle graspers, or the like. Instead, the end effector 40 can be in the form of a single working element arrangement, such as, for example, an electrocautery electrode, a scalpel, or the like. It will be appreciated that the surgical instrument 28 is described by way of example only, and need not necessarily have a wrist member, but could be mounted directly on the end 31 of the shaft 28.1 instead.

Figure 3:
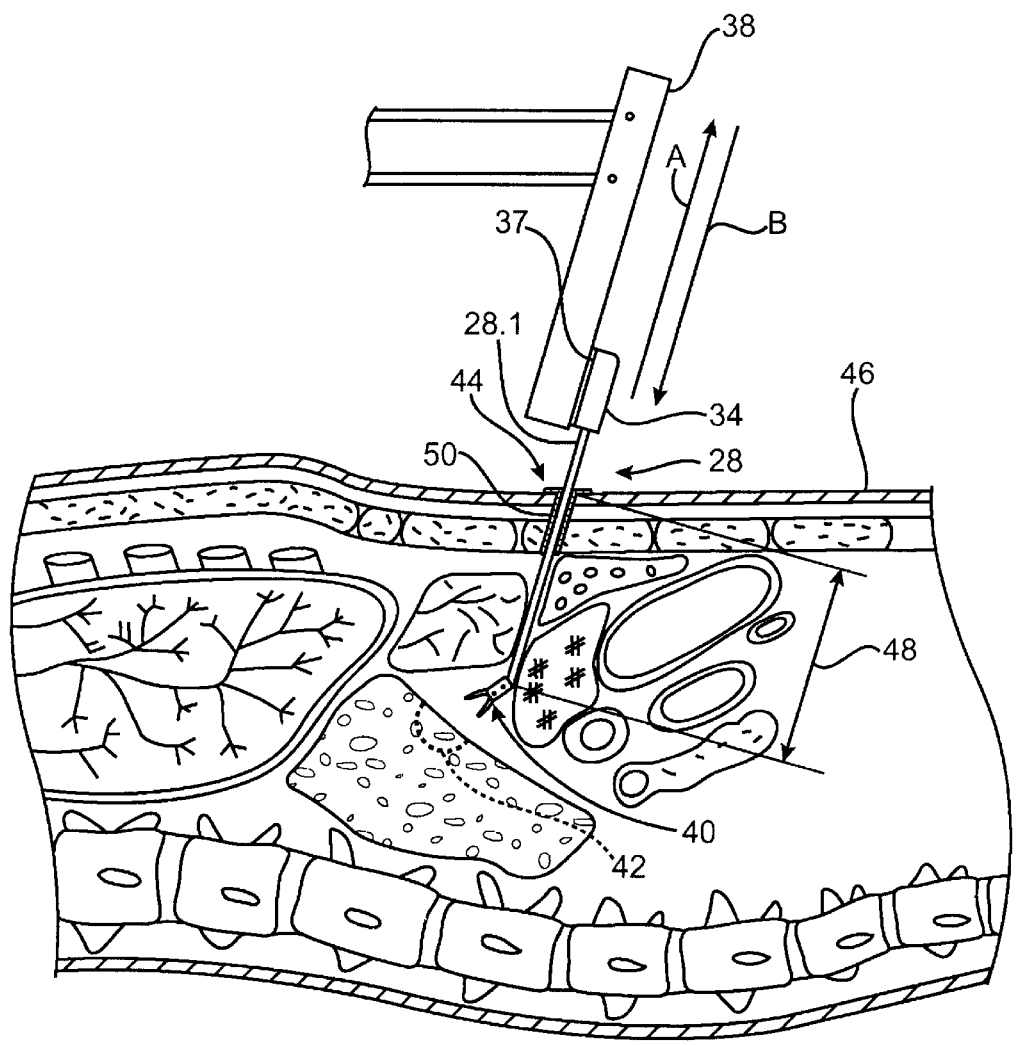
FIG. 3 shows a schematic side view of a surgical instrument similar to the surgical instrument of FIG. 2 being used to perform a surgical task by means of the telesurgical system of FIG. 1.

Referring now to FIG. 3 of the drawings, in which like reference numerals are used to designate similar parts, unless otherwise stated, a selected surgical instrument 28 having a specific end effector 40 required to perform a specific surgical task during a surgical procedure is shown. In use, the end effector 40 of the surgical instrument 28 is typically introduced to an internal surgical site, schematically indicated at 42, through an aperture 44 in a patient body 46. The aperture 44 can be in the form of a naturally occurring body aperture, or, as is more typically the case, it can be in the form of an incision made to permit the end effector 40 to be inserted therethrough so as to be introduced to the surgical site 42. The end effector is typically inserted through the aperture 44 and is then navigated through part of the patient body, generally indicated at 48, to be positioned in close proximity to the surgical site 42. A cannula sleeve 50 can be positioned in the aperture 44 to retain it in an open condition, for example.

During the course of the surgical procedure, it can happen that the specific surgical instrument 28 needs to be replaced with another surgical instrument, similar to the surgical instrument 28, but bearing a different end effector appropriate for performing a different surgical task.

To exchange, or replace, the surgical instrument 28 with another surgical instrument, the surgical instrument 28 is typically withdrawn from the surgical site 42, and from the patient body 46, as indicated by arrow A. Once the surgical instrument 28 is clear of the patient body 46, it is typically dismounted from the carriage 37. Another surgical instrument bearing the desired end effector can then be mounted on the carriage 37 and can then be introduced to the surgical site 42 by passing the end effector through the aperture 44, as indicated by arrow B, navigating the end effector from the aperture 44 through the part 48 of the patient body 46 until it is positioned in close proximity to the surgical site 42. The replacement surgical instrument can be introduced to the surgical site 42 in this manner by mounting it on the carriage 37 and introducing it to the surgical site 42 while mounted on the carriage 37. However, it will be appreciated that the surgical instrument can be introduced to the surgical site 42 independently of being mounted on the carriage 37 so that when the surgical instrument is positioned so that its end effector is in close proximity to the surgical site 42, it can then be coupled to the carriage 37.

It has been found that when the surgical instrument is introduced to the surgical site 42 in this manner, difficulty can be experienced in navigating it through the part 48 of the patient body 46.

Figure 4:
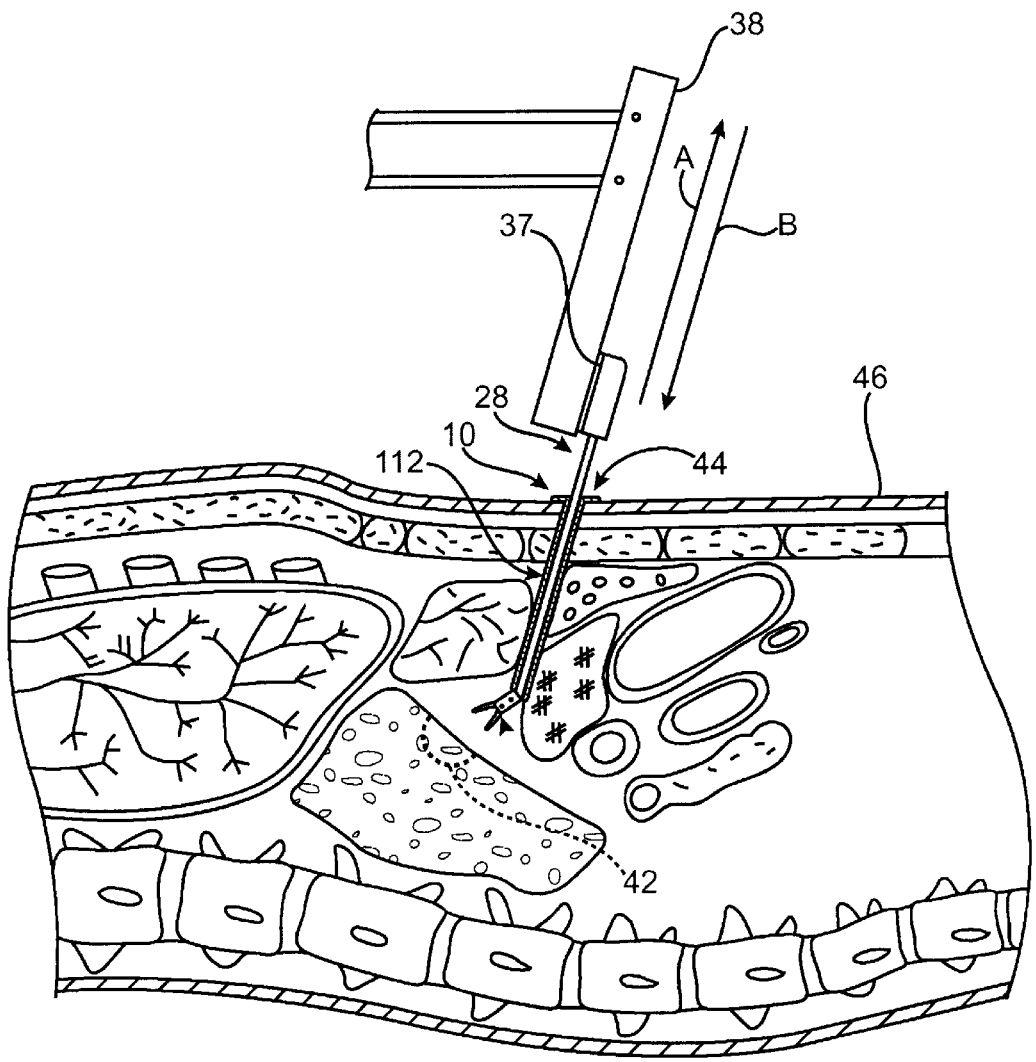
FIG. 4 shows a schematic side view corresponding to FIG. 3, an end effector of the surgical instrument having been introduced to an internal surgical site by means of a tool guide in accordance with the invention.
Figure 5:
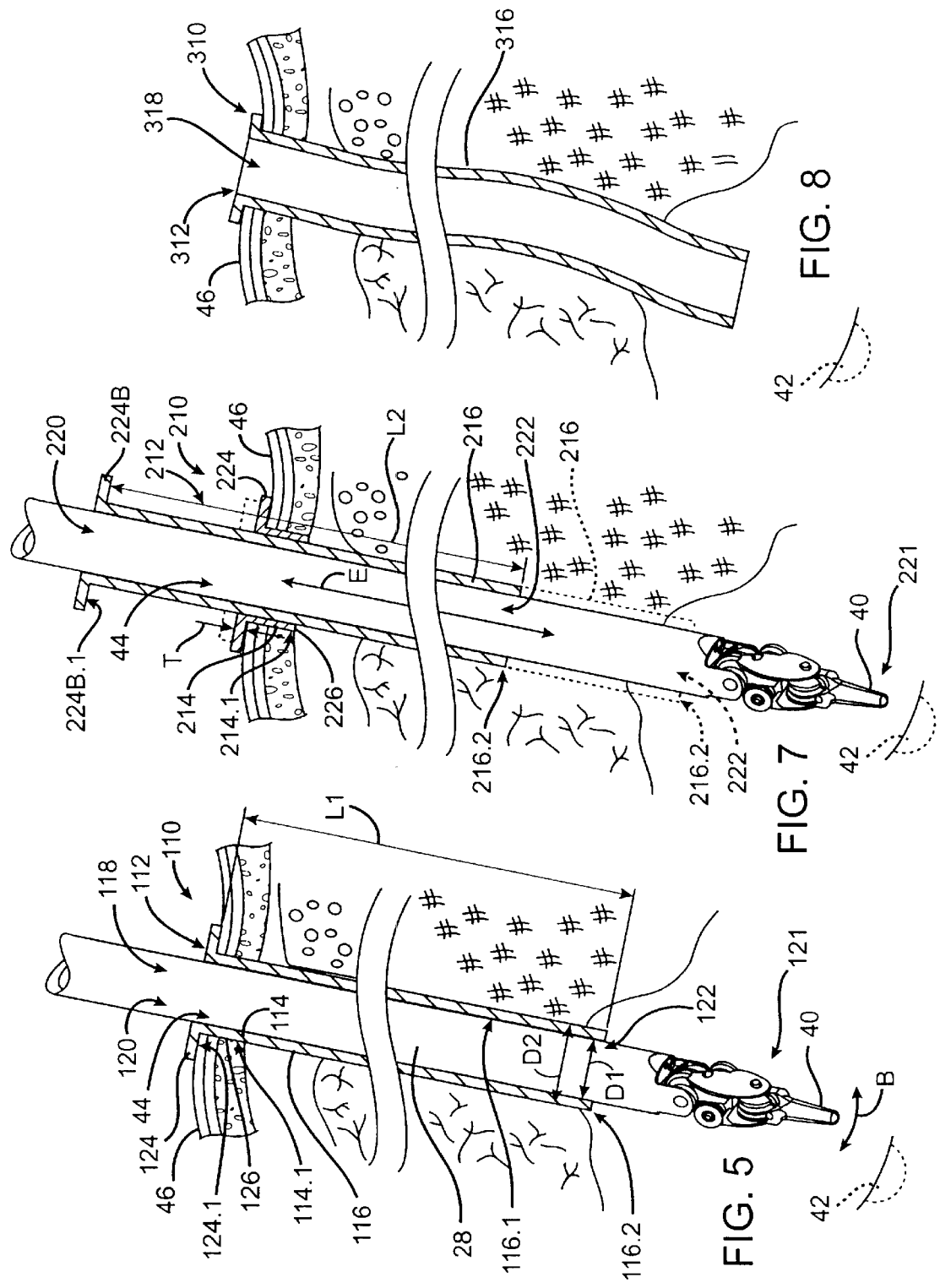
FIG. 5 shows, at an enlarged scale, a schematic sectional side view of the tool guide shown in FIG. 4.

FIGS. 4 and 5 illustrate one embodiment of a tool guide in accordance with the invention, which is generally indicated by reference numeral 110. In FIGS. 4 and 5, like reference numerals are used to designate similar parts, unless otherwise stated. To ease the task of introducing the end effector of a surgical instrument to the surgical site 42, use can be made of a tool guide in accordance with the invention.

The tool guide 110 is arranged to guide an end effector of a robotically controllable surgical instrument from a position outside the patient body 46 to a position in close proximity to an internal surgical site within the patient body 46. The tool guide 110 typically includes a tool guide body generally indicated by reference numeral 112. A seat formation 114 on the body 112 is provided. The seat formation 114 is arranged to seat in the aperture 44 leading into the patient body 46 so as to mount the body 112 on the patient body 46. The tool guide 110 further comprises a sheath formation 116 on the body 112. The sheath formation 116 defines a longitudinally extending internal passage 118, an inlet or entry port 120 leading into the passage 118, and an outlet or exit port 122 leading from the passage 118. The ports 120, 122, and the passage 118, are sized to permit the end effector 40 of the surgical instrument 28 to be passed through the entry port 120, along the internal passage 118, and out from the exit port 122. The sheath formation 116 is arranged to cooperate with the seat formation 114 such that when the seat formation 114 is seated in the aperture 44, the exit port 122 of the sheath formation 116 can be positioned in close proximity to the internal surgical site 42, while the entry port 120 is accessible from outside the patient body 46, thereby to enable the end effector 40 to be guided to a position, indicated at 121, in close proximity to the surgical site 42, by passing the end effector 40 through the entry port 120, along the internal passage 118, and out from the exit port 122, so as to emerge from the exit port 122 at the position 121 in close proximity to the internal surgical site 42.

The sheath formation 116 is typically in the form of a round cylindrical tubular portion. The internal passage 18 is defined between a longitudinally extending inner wall 116.1 of the sheath formation, the inner wall 116.1 having a predetermined internal diameter. The sheath formation 116 preferably has an internal diameter D1 providing sufficient clearance to allow passage of the tool, and more preferably without excessive clearance to avoid substantial loss of insufflation gas, typically falling in the range between about 3 mm and about 20 mm. Advantageously, the sheath formation has an internal diameter D1 of about 5 to 12 mm.

The sheath formation 116 typically has an outer diameter D2 falling in the range between about 4 mm and about 26 mm sufficient to provide structural strength, typically. Advantageously, the outer diameter D2 can be about 6 to 14 mm.

The tool guide 110 further comprises a stop 124 on the body 112. The stop 124 is arranged to seat against the patient body 46 when the seat formation 114 is seated in the aperture 44. The stop 124 can be in the form of any appropriate laterally directed protrusion. By way of example only, and as indicated in the drawings, the stop 124 can be in the form of a radially outwardly protruding stop flange.

Advantageously, the sheath formation 116 can have an operative length L1 extending between an inner face 124.1 of the stop flange falling in the range between about 25 mm and about 250 mm.

The tool guide 110 further includes a round cylindrical tubular portion 126. The seat formation 114 is defined by an outer surface 114.1 of the round cylindrical tubular portion. It will be appreciated that the round cylindrical portion 126 defining the seat formation 114 is defined by part of the round cylindrical portion defining the sheath formation 116.

In use, the tool guide 110 is inserted through the aperture 44 until the stop 124 abuts against the patient body 46. The exit port 122 can then be positioned in close proximity to the surgical site 42, by, for example, moving the sheath formation angularly about the aperture 44 as indicated by arrows B. The end effector 40 can then be passed through the entry port 120 and guided along the internal passage 118 until it emerges from the exit opening 122 to be in the position 121 in which it is in close proximity to the site 42.

When it is desired to replace the instrument 28 with an instrument having another type of end effector, the surgical instrument 28 is withdrawn from the patient body 46 whilst the tool guide 110 remains in a mounted condition on the body 46. After the instrument 28 has been removed, a new instrument, having a desired end effector, can be introduced to the surgical site 42 by passing its end effector through the entry port 120, along the internal passage 118, and out from the exit port 122.

It will be appreciated that during such a tool exchange operation, the tool guide 110 remains in a mounted condition on the patient body 46. In this manner, surgical instruments can be exchanged with relative ease and expediency and the part of the patient body 48 is protected from inadvertent injury.

The length L1 of the tool guide 110 is determined by the depth, or distance, between the surgical site 42 and the aperture 44 leading into the patient body. Accordingly, for typical surgical sites, the tool guide 110 may have a length L1 falling in the said range between about 25 mm and about 250 mm mentioned above. Typically, a plurality of tool guides, similar to the tool guide 110, can be supplied, each tool guide being similar to the other, save that the lengths L1 of the different tool guides vary. Accordingly, the invention extends to a tool guide kit comprising a plurality of tool guides having different sheath formation lengths so that an appropriate tool guide 110 which has a suitable length L1 determined by the depth, or distance, between the surgical site 42 and the aperture 44, can be selected from the kit.

Figure 6:
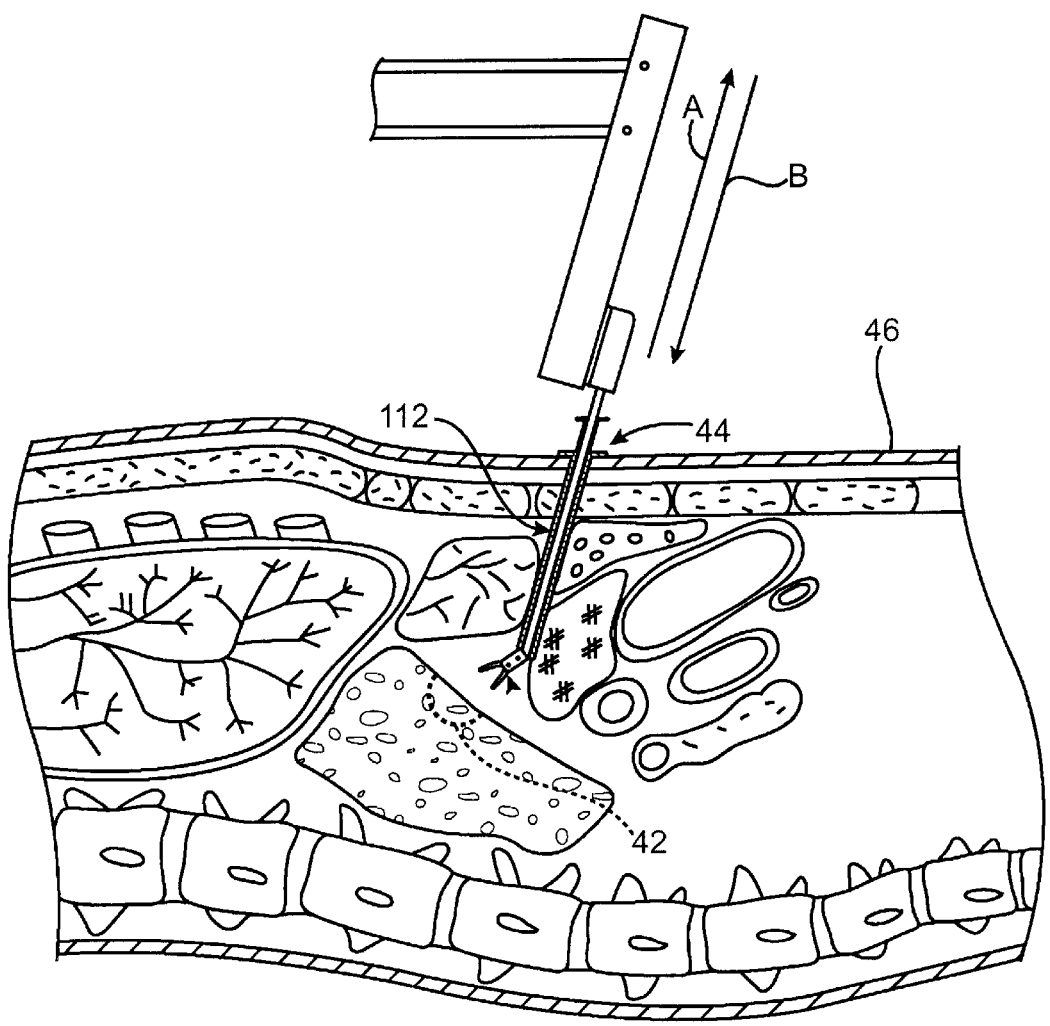
FIG. 6 shows a schematic side view corresponding to FIG. 3, an end effector of the surgical instrument having been introduced to the internal surgical site by means of another tool guide in accordance with the invention.

Referring now to FIGS. 6 and 7 of the drawings, in which like reference numerals are used to designate similar parts, unless otherwise stated, another embodiment of the tool guide in accordance with the invention is generally indicated by reference numeral 210.

The tool guide 210 includes a tool guide body generally indicated by reference numeral 212. The body 212 includes a sheath formation 216 similar to the sheath formation 116 of the tool guide 110. The body 212 further includes a round cylindrical portion 226 which has an outer surface 214.1 defining a seat formation 214. It will be appreciated that the seat formation 214 is similar to the seat formation 114, save that the seat formation 214 is not defined by part of the cylindrical tubular portion of the sheath formation 216, but is defined on a separate cylindrical tubular portion.

The tubular portion 226 defines a stop 224 arranged to seat against the patient body 46 when the seat formation 214 is seated in the aperture 44. The stop 224 can be in the form of any appropriate laterally directed protrusion. By way of example only, and as indicated in the drawings, the stop 224 can be in the form of a radially outwardly protruding stop flange.

The sheath formation 216 is axially displaceably received in the cylindrical tubular portion 226 as indicated by the double headed arrow E. When the portion 226 is seated in the aperture 44, the sheath formation 216 is selectively displaceable between an extended condition, indicated in dashed lines in FIG. 7, and a withdrawn condition, indicated in solid lines in FIG. 7. The sheath formation 216 has a sheath stop 224B so as to inhibit the sheath formation 216 from being axially displaced relative to the portion 226 beyond a predetermined distance. The sheath stop 224B can be in the form of any appropriate laterally outwardly directed protrusion. By way of example only, and as indicated in the drawings, the sheath stop can be in the form of a radially outwardly protruding sheath flange.

The sheath formation 216 can have an operative length L2 extending between an inner face 224B.1 of the sheath stop 224B, which inner face 224B.1 faces in the direction of the sheath formation 216, and an opposed end 216.2 of the sheath formation 216, which opposed end defines an exit port 222, plus an amount equal to a thickness T of the stop 224.

In use, the body 212 of the tool guide 210 is mounted on the patient body 46 by inserting the portion 226 into the aperture 44 such that the seat formation 214 is seated in the aperture 44 and the stop 224 is seated against the patient body 46. When it is desired to introduce the end effector 40 of the tool 28 to the surgical site 42, the sheath formation 216 is displaced relative to the portion 226 into its extended condition. The end effector 40 is then passed through an entry port 220 defined by the sheath formation 216, guided along an internal passage 218 defined within the sheath formation 216 and out from the exit port 222, so as to emerge from the exit port 222 at a position 221 in close proximity to the surgical site 42. When the end effector 40 has been introduced in this manner, the sheath 216 can be displaced into its withdrawn condition. When it is then desired to replace the surgical instrument with another surgical instrument having a different end effector, the sheath formation 216 is displaced into its extended condition. The tool to be replaced is removed from the patient body and another surgical instrument bearing the desired end effector is inserted through the entry port 220, along the passage 218, and out from the exit port 222 so as to be positioned in close proximity to the surgical site 42. When the new surgical instrument has been introduced to the surgical site in this manner, the sheath formation 216 can again be displaced into its withdrawn condition.

Referring now to FIG. 8 of the drawings, in which like reference numerals are used to designate similar parts, unless otherwise stated, another embodiment of a tool guide in accordance with the invention is generally indicated by reference numeral 310. The tool guide 310, which includes a tool body 312 and a sheath formation 316, is similar to the tool guide 110 save that at least its sheath formation 316 is made of a resiliently deformable, preferably bio-compatible, material. Conveniently, the entire tool guide 310 can be made of a resiliently deformable bio-compatible material.

In use, the tool guide 310 is used in similar fashion to the tool guide 110. However, when a shaft of a surgical instrument is not received within its passage 318, the sheath formation 316 can flex, or deform resiliently, in sympathy with pressures exerted thereon within the patient body 46.

Figure 9:
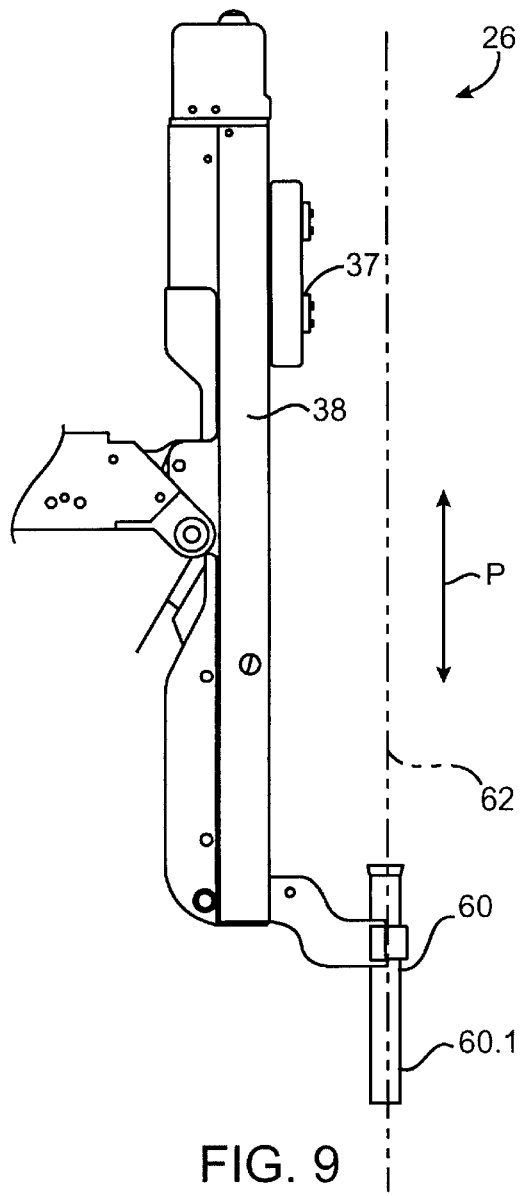
FIG. 9 shows a schematic side view of an end portion of a robotic arm.
Figure 10:
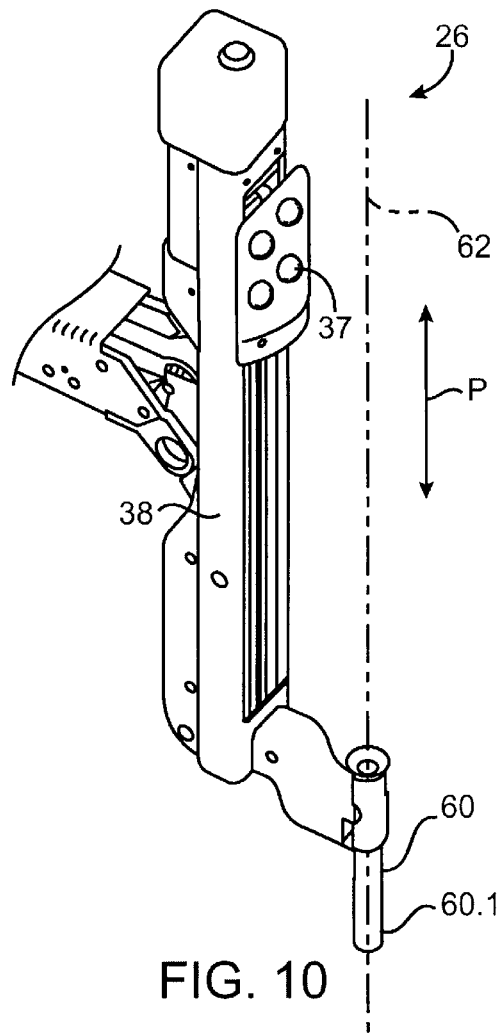
FIG. 10 shows a schematic three-dimensional view of the end portion of the robotic arm shown in FIG. 9.

Another aspect of the invention will now be described with reference to FIGS. 1, 2, and 9 to 13. Referring initially to FIGS. 9 and 10, a surgical instrument, similar to the one shown in FIG. 2 for example, of a robotic surgical system can be introduced to an internal surgical site using a guide or cannula-like formation 60 on the robotic arm. The robotic arm, which can be similar to the one indicated at 26 in FIG. 1 for example, can then be maneuvered relative to an aperture leading into the patient body so as to mount the guide, or cannula-like formation 60 of the robotic arm, within the aperture. The guide 60 on the arm can typically be in the form of a tubular member. The surgical instrument can then be fed into the patient body by passing the end effector through the guide 60 so as to pass through the aperture in the patient body. A shaft of the instrument is then typically axially aligned with an axis 62 defined on the arm 26.

It has been found that to maneuver the robotic arm in this fashion so as to locate the guide 60 in the aperture can be rather cumbersome. Another tool guide, in accordance with the invention, for assisting in the locating of the robotic arm relative to the aperture will now be described with reference to FIGS. 11–13.

Figure 11:
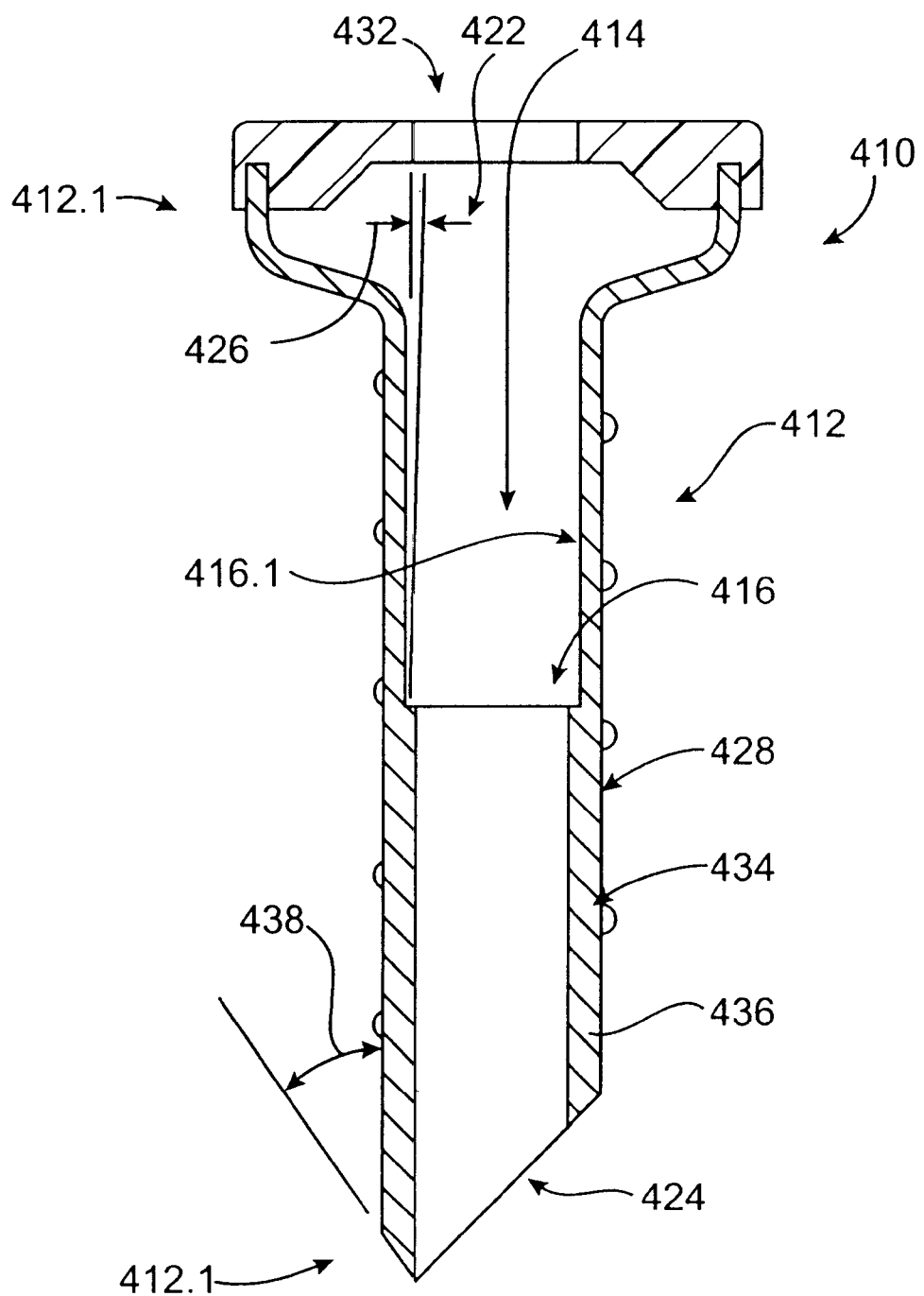
FIG. 11 shows a schematic sectional side view of another tool guide in accordance with the invention.

Referring initially to FIG. 11, the tool guide is generally indicated by reference number 410. The tool guide 410 comprises an elongate body, generally indicated by reference numeral 412. The body 412 defines opposed ends 412.1, 412.2. It further comprises a passage 414 extending longitudinally along the body 412 between the opposed ends 412.1, 412.2. The tool guide 410 further comprises an engaging formation, generally indicated by reference number 416, on the body 412. The engaging formation 416 is arranged to cooperate with a complimentary engaging formation on the robotic arm so that the tool guide 410 can be mounted in an aperture leading into a patient body and the robotic arm can then be coupled to the tool guide 410 while the tool guide is mounted in the aperture.

The engaging formation 416 is typically in the form of a socket formation. The socket formation is defined within the passage 414 of the tool guide 410. When mounted in an aperture 418 leading into a patient body 420, as can best be seen with reference to FIGS. 12 and 13, an inlet 422 of the tool guide 410 which leads into the passage 414 is arranged to be accessible from outside the patient body 420 when the tool guide 410 is mounted in the aperture 418. An outlet 424 which leads from the passage 414 is arranged to be positioned within the patient body 420 when the tool guide 410 is mounted on the patient body. The socket formation 416 is positioned adjacent the inlet 422.

The socket formation 416 can typically comprise a circumferentially extending surface 416.1 which defines at least part of the passage 414. Conveniently, the surface 416.1 can taper inwardly in a direction away from the inlet 422 as indicated at 426.

The tool guide 410 further comprises an outer surface 428. The outer surface 428 defines at least one gripping formation 430 arranged to be gripped by tissue when the tool guide 410 is mounted on the patient body 420 so as to hold it in place when in its mounted condition on the patient body. The gripping formation 430 can comprise a rib extending helically around the outer surface 428 as indicated in the drawings. However, any appropriate gripping formation can be provided such as, for example, a plurality of ribs extending around the outer surface 428, a plurality of bumps, or knobs, or the like, or even by providing the surface 428 with a roughened or knurled texture.

Referring again to FIG. 11 of the drawings, the tool guide 410 further comprises a sealing formation 432 which sealingly covers the inlet 422. The sealing formation 432 is arranged to permit the engaging formation of the robotic arm to pass therethrough, as will be described in greater detail hereinbelow. Typically, the sealing formation 432 is at least partially formed from a synthetic plastics material such as silicone, or the like. The elongate body 412 can typically be made of steel, such as surgical steel, or the like. Instead, the body 412 can be made of any appropriate material which is preferably biocompatible, such as an appropriate synthetic plastics material, or the like.

The tool guide 410 further comprises a cross-sectionally circular tubular portion 434 which defines the outlet 424 at the end 412.2. A wall 436 of the tubular portion 434 defines a taper formation which tapers outwardly in a rearward direction away from the outlet 424 as indicated at 438.

Figure 12:
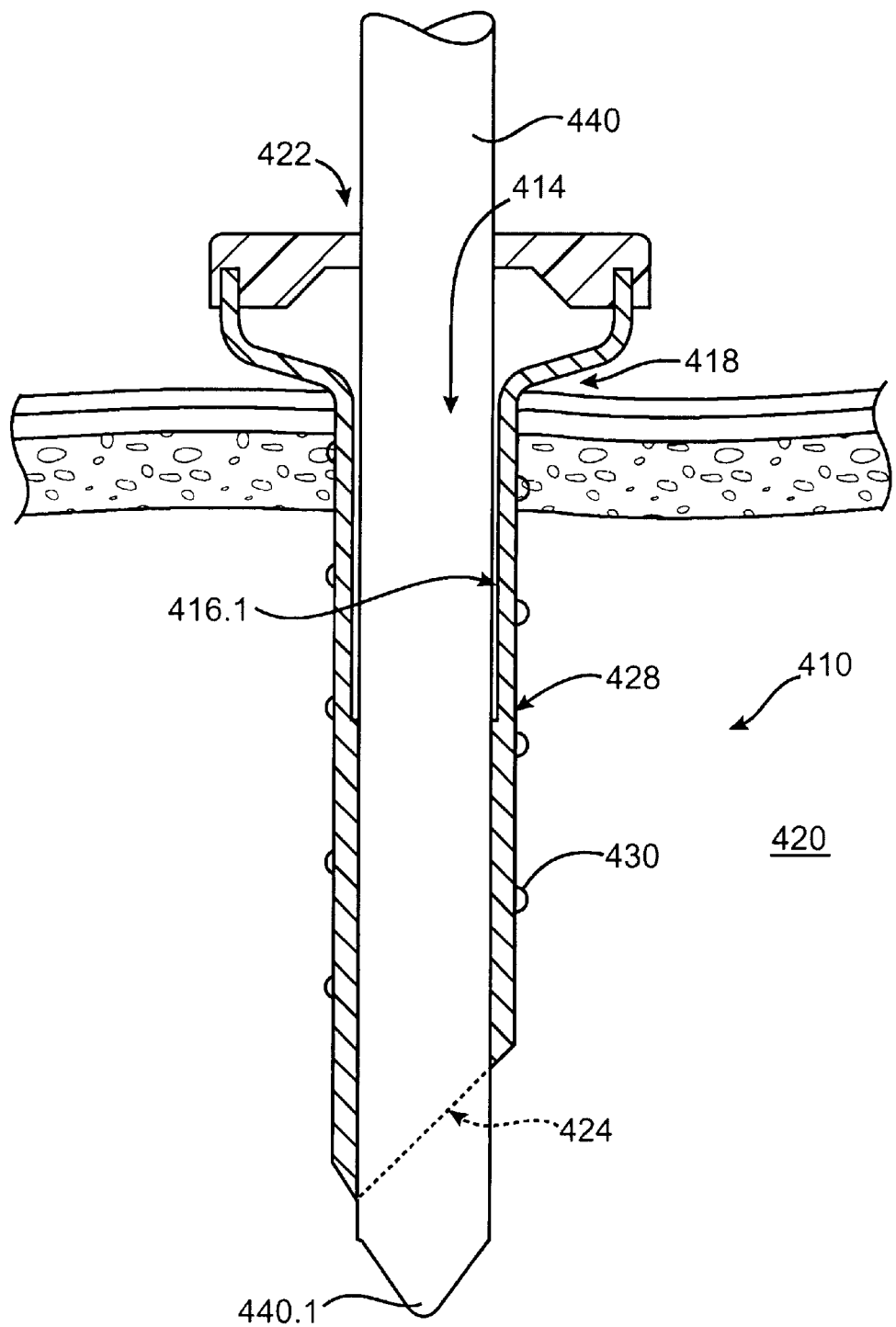
FIG. 12 shows a schematic sectional side view of the tool guide of FIG. 11 being passed through an aperture in a patient body.
Figure 13:
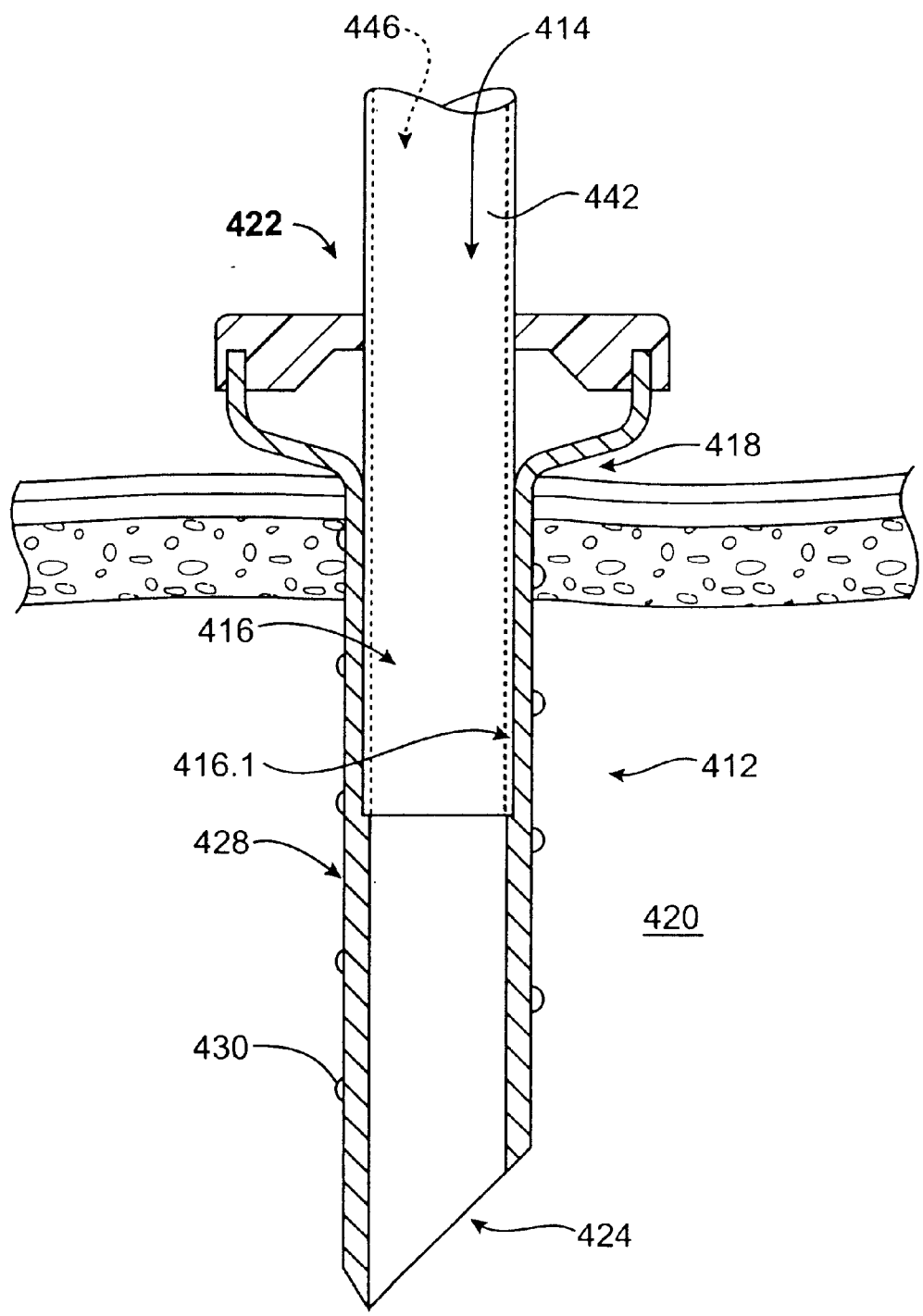
FIG. 13 shows a schematic sectional side view of the tool guide of FIGS. 11 and 12 in a mounted condition in an aperture leading into a patient body, the tool guide being engaged to an engaging formation on a robotic arm.

To mount or locate the tool guide 410 in the aperture 418, use can typically be made of an obturator 440, as can best be seen in FIG. 12. This is achieved by locating the obturator 440 within the passage 414 such that a leading end 440.1 of the obturator 440 protrudes from the outlet 424. The outlet 424 of the tool guide 410 is then passed through the aperture 418 while the leading end 440.1 of the obturator 440 protrudes from the outlet 424. The tapered formation 438 assists in parting tissue as the guide 410 is inserted into the patient body through the aperture 418. When the tool guide 410 is mounted on the patient body, as indicated in FIGS. 12 and 13, the obturator 440 is withdrawn from the passage leaving the tool guide 410 in a mounted condition on the patient body. The gripping formation 430 then assists in holding the guide 410 in place on the patient body.

Once the tool guide 410 is mounted on the patient body, and as can best be seen with reference to FIG. 13, the tool guide 410 is then coupled to a robotic arm while the tool guide 410 is mounted in the aperture 418. This is achieved by inserting an engaging formation 442 on the robotic arm into the socket formation 416. Engaging the engaging formation 442 on the robotic arm in the socket 416 in this fashion, comprises passing the engaging formation 442 through the sealing formation 432.

The engaging formation 442 can be similar to the guide 60 shown in FIGS. 9 and 10, in which case an outer surface 60.1 of the guide 60 seats snugly against the tapering surface 416.1 of the socket formation 416 when engaged therewith. The engaging formation 442, or guide 60, typically comprises a passage 446 extending axially therethrough. When the engaging formation 442, or guide 60, is engaged with the tool guide 410 the passage 446 is in register with the passage 414 of the tool guide 410.

When the engaging formation 442, or guide 60, has been engaged with the tool guide 410 in this fashion, at least part of a surgical procedure can be performed with a robotically-controlled surgical instrument operatively connected to a robotic arm and extending through the tool guide 410. The surgical instrument can be similar to the instrument shown in FIG. 2 and accordingly can comprise a shaft and an end effector operatively mounted on one end of the shaft. To perform the surgical procedure, the end effector is typically passed through the inlet 422 along the passage 414 and out from the outlet 424 so that the shaft of the instrument extends through the inlet 422, along the passage 414 and out from the outlet 424.

The surgical instrument can be operatively connected to the robotic arm prior to passing the end effector through the inlet 422. Instead, the surgical instrument can first be positioned to extend through the tool guide 410 and can then be operatively connected to the robotic arm.

The tool guide 410 can have a length similar to the length of the tool guides 110, 310 of FIGS. 5 and 8 respectively. Furthermore, it will be appreciated that the tool guides 110, 310 can be provided with an engaging formation 416 so that when these tool guides are positioned to extend through an aperture in the patient body, a robotic arm can thereafter be coupled to them in a fashion as described above with reference to tool guide 410. Furthermore, the tool guides 110, 210, 310 can be provided with sealing formations 432, tapered end formations 438, gripping formations 430, and the like, similar to those described above.

With reference to FIG. 7, the tool guide 210 can be arranged such that the seat formation 224 is mounted on the robotic arm in a fashion similar to the guide formation 60 shown in FIGS. 9 and 10. In such a case, the seat formation on the arm is positioned in the aperture by maneuvering the arm. The sheath formation 216 can then selectively be extended into and withdrawn from the patient body by displacing it relative to the robotic arm and the seat formation 224.

A method of the invention of preparing for robotic surgery comprises first determining one or more locations in a patient's body surface for the placement of incisions or "ports" for insertion of tools for a robotic surgical procedure. This may be done as part of the pre-operative planning and set-up, before beginning invasive surgical operations.

An incision may then be made for each such determined port location, and a tool guide as described herein (e.g., guide 410, shown in FIGS. 11–13) may be inserted into the incision, the guide preferably including a sealing formation as described herein (e.g., sealing formation 432), the sealing formation being configured to seal the insertion aperture or inlet 422 of the guide. The sealed guide may thus prevent loss of insufflation gas from the body cavity prior to insertion of a tool through the guide.

In the event that a greater number of ports may be desired, than the number of robotic arms to be employed for the surgical procedure, (e.g., to allow one arm to manipulate tools from more than one port location), these additional port placement location may be planned and tool guides pre-placed and sealed prior to beginning robotic operation. The ports may optionally include ports for non-robotic tools to be cooperatively employed in the procedure, such as non-robotic tissue retractors, accessory supports, tissue stabilizers, irrigation or suction devices and the like.

Subsequently, tools may be inserted and seated into the pre-placed tool guides when needed to perform the surgical procedure. A tool may thus be exchanged between one such sealable tool guide and another pre-placed sealable guide as needed. Alternatively, a tool/robotic arm assembly may be removed from one such sealable tool guide, the tool replaced by a substitute tool on the robotic arm, and the substitute tool inserted in a second such pre-placed sealable tool guide.

It has been found that providing a tool guide with a sealing formation as described above can be advantageous. This is especially true when the surgical procedure is to be performed within a body cavity and where the cavity is to be insufflated, and where at least one arm of a robotic surgical system needs to be located relative to different apertures leading into the patient body during the course of the surgical procedure. In such a case, a plurality of tool guides each having a sealing formation, such as the sealing formation 432 described above, can be mounted on the patient body at predetermined positions so that an instrument can selectively be located in any one of the tool guides using the same robotic arm. In this fashion, an instrument on one arm can be passed through one tool guide to perform part of the surgical procedure, and once that part of the surgical procedure has been completed, the instrument can be withdrawn and the same arm can be used to pass the same or another instrument through another tool guide so as to perform another part of the surgical procedure. The sealing formations 432 on the tool guides then inhibit loss of insufflation between removing an instrument from one aperture and passing it through another.

While exemplary embodiments have been described in some detail, for clarity of understanding and by way of example, a variety of modifications, changes, and adaptations will be obvious to those with skill in the art. For example, although reference has been made to a specific type of surgical instrument 28, the invention is not limited to use with such an instrument only, but extends to use with any robotically controlled surgical instrument to be introduced to an internal surgical site. Therefore, the scope of the present invention is to be limited solely by the appended claims.

What is claimed is:

1. A method of performing a surgical procedure, the method comprising:

locating a sheath formation in a mounted condition in an aperture leading into a patient body, the sheath formation defining a passage, an inlet leading into the passage and an outlet leading from the passage, the inlet being accessible from outside the patient body when the sheath formation is in its mounted condition;

positioning the sheath formation in an extended condition, in which the outlet is positioned in close proximity to a surgical site within the patient body;

passing an end effector of a robotically controllable surgical instrument through the inlet, along the passage and out from the outlet, so as to emerge from the outlet at a position in close promixity to the surgical site;

displacing the sheath formation, when the end effector is positioned in close proximity to the surgical site, from the extended position into a withdrawn condition, in which the outlet is withdrawn from the surgical site; and robotically controlling the surgical instrument to cause the end effector to perform at least part of a surgical procedure at the surgical site.

2. The method of claim 1, wherein the sheath formation defines a stop, locating the sheath formation in its mounted condition in the aperture comprising inserting the sheath formation through the aperture until the stop seats against the patient body.

3. The method of claim 1, further comprising:

displacing the sheath formation from its withdrawn condition into its extended condition;

withdrawing the surgical instrument from the patient body; and positioning an end effector of another surgical instrument at a position in close proximity to the surgical site by passing the end effector through the inlet, along the passage and out from the outlet of the sheath while in its extended condition so as to emerge from the outlet at the position in close proximity to the surgical site.

4. The method of claim 1, wherein the sheath formation forms part of a tool guide, the tool guide further comprising a seat formation seatable in the aperture leading into the patient body so as to mount the sheath on the patient body, the sheath formation being axially displaceable relative to the seat formation; and the step of displacing the sheath formation between its extended condition and its withdrawn condition comprises displacing the sheath formation axially relative to the seat formation.

5. The method of claim 1, wherein the sheath formation is of a resiliently deformable material, the method comprising:

removing the surgical instrument from the patient body;

permitting the sheath formation to deform in sympathy with pressure inside the patient body; and introducing an end effector of another surgical instrument to the surgical site by passing the end effector of the other surgical instrument through the inlet, along the passage and out from the outlet, so as to emerge from the outlet at a position in close proximity to the surgical site.

6. A method as claimed in claim 1, in which the sheath formation is defined by a tool guide, the method comprising the prior steps of determining a distance between the aperture leading into the patient body and the surgical site; and selecting a tool guide having a particular length from a tool guide set including a plurality of tool guides having a variety of different sheath formation lengths, so as to obtain a tool guide having a sheath formation length corresponding to the distance between the aperture leading into the patient body and the surgical site, so that when the sheath formation of the selected tool guide is located in a mounted condition on the patient body, its outlet is positionable in closing proximity to the surgical site.

7. A method of performing a robotically controlled surgical procedure, the method comprising:

mounting a tool guide in an aperture leading into a patient body, the tool guide defining a passage extending from an inlet of the tool guide to an outlet of the tool guide, the inlet being accessible from outside the patient body and the outlet being positioned within the patient body when the tool guide is mounted in the aperture;

coupling the tool guide to a robotic arm while the tool guide is mounted in the aperture; and performing at least part of a surgical procedure with a robotically controlled surgical instrument operatively connected to the robotic arm and extending through the inlet, along the passage and out from the outlet of the tool guide.

8. The method of claim 7, wherein the surgical instrument comprises a shaft and an end effector operatively mounted on one end of the shaft; and the method comprises passing the end effector of the surgical instrument through the inlet, along the passage and out from the outlet of the tool guide so that the shaft of the instrument extends through the inlet, along the passage and out from the outlet of the tool guide.

9. The method of claim 7, which comprises operatively connecting the surgical instrument to the robotic arm prior to passing the end effector through the inlet along the passage and out from the outlet of the tool guide.

10. The method of claim 7, which comprises operatively connecting the surgical instrument to the robotic arm after passing the end effector through the inlet along the passage and out from the outlet of the tool guide.

11. The method of claim 7, wherein the tool guide has an engaging formation and the robotic arm has a complementary engaging formation, and wherein the step of coupling the tool guide to the robotic arm comprises engaging the engaging formation of the robotic arm with the engaging formation of the tool guide.

12. The method of claim 11, wherein the engaging formation of the tool guide comprises a socket formation and the engaging formation of the robotic arm is arranged to be received in the socket formation; and
wherein the step of engaging the engaging formation of the robotic arm with the engaging formation of the tool guide comprises inserting the engaging formation of the robotic arm into the socket formation.

13. The method of claim 11, wherein the tool guide has a sealing formation sealingly covering the inlet, and the step of engaging the engaging formation of the robotic arm with the engaging formation of the tool guide comprising passing the engaging formation of the robotic arm through the sealing formation.

14. The method of claim 11, wherein the engaging formation of the robotic arm is defined by a guide for guiding the surgical instrument on the robotic arm, the guide comprising a passage, the passage of the guide being in register with the passage of the tool guide when the engaging formation of the robotic arm is engaged with the engaging formation of the tool guide; and
the method further comprising passing the end effector through the passage of the guide and then through the passage of the tool guide.

15. The method of claim 7, wherein performing at least part of the surgical procedure with the robotically controllable surgical instrument comprises causing the robotic arm to move in response to movement of a master control device operatively associated with the robotic arm.

16. The method of claim 7, wherein mounting the tool guide on the patient body comprises passing the outlet of the tool guide through an incision in the patient body.

17. The method of claim 7, which comprises positioning an obturator within the passage of the tool guide such that a leading end of the obturator protrudes from the outlet, passing the outlet of the tool guide through the incision in the patient body while the leading end of the obturator protrudes from the outlet, and withdrawing the obturator from the passage when the tool guide is mounted on the patient body.

18. The method of claim 7, which comprises the prior step of selecting the tool guide from a plurality of tool guides including guides having a variety of different lengths, so that the tool guide has a length such that when mounted on the patient body the outlet is positioned in close proximity to a surgical site at which the at least part of the surgical procedure is to be performed.

19. The method of claim 7, further comprising:
mounting a plurality of tool guides on the patient body; and,
decoupling the robotic arm from one tool guide and coupling the robotic arm to another tool guide; and
performing another part of the surgical procedure with a robotically controlled surgical instrument operatively mounted on the robotic arm and extending through the inlet, along the passage and out from the outlet of the other tool guide.

20. The method of claim 19, wherein each tool guide has a sealing formation arranged sealingly to cover its inlet, the method comprising permitting the sealing formations on the tool guides sealingly to cover their inlets in the absence of a surgical instrument extending through their inlets.

21. A method of performing a surgical procedure, the method comprising:
locating a sheath formation in a mounted condition in an aperture leading into a patient body, the sheath formation defining a passage, an inlet leading into the passage and an outlet leading from the passage, the inlet being accessible from outside the patient body when the sheath formation is in its mounted condition, wherein the sheath formation is of a resiliently deformable material;
positioning the outlet in close proximity to a surgical site within the patient body;
passing an end effector of a robotically controllable surgical instrument through the inlet, along the passage and out from the outlet, so as to emerge from the outlet at a position in close proximity to the surgical site;
robotically controlling the surgical instrument to cause the end effector to perform at least part of a surgical procedure at the surgical site;
removing the surgical instrument from the patient body;
permitting the sheath formation to deform in sympathy with pressure inside the patient body; and
introducing an end effector of another surgical instrument to the surgical site by passing the end effector of the other surgical instrument through the inlet, along the passage and out from the outlet, so as to emerge from the outlet at a position in close proximity to the surgical site.

22. A method of performing a surgical procedure, the method comprising:
determining a distance between an aperture leading into a patient body and a surgical site;
selecting a tool guide having a particular length from a tool guide set including a plurality of tool guides having a variety of different sheath formation lengths, so as to obtain a tool guide having a sheath formation length corresponding to the distance between the aperture leading into the patient body and the surgical site, so that when a sheath formation of the selected tool guide is located in a mounted condition on the patient body, an outlet of the tool guide is positionable in close proximity to the surgical site
locating the sheath formation in the mounted condition in the aperture leading into the patient body, the sheath formation defining a passage, an inlet leading into the passage and the outlet leading from the passage, the inlet being accessible from outside the patient body when the sheath formation is in its mounted condition;
positioning the outlet in close proximity to a surgical site within the patient body;
passing an end effector of a robotically controllable surgical instrument through the inlet, along the passage and out from the outlet, so as to emerge from the outlet at a position in close proximity to the surgical site; and
robotically controlling the surgical instrument to cause the end effector to perform at least part of a surgical procedure at the surgical site.

* * * * *

UNITED STATES PATENT AND TRADEMARK OFFICE
CERTIFICATE OF CORRECTION

| | | |
|---|---|---|
| PATENT NO. | : 6,620,173 B2 | |
| APPLICATION NO. | : 09/872750 | |
| DATED | : September 16, 2003 | |
| INVENTOR(S) | : Craig Richard Gerbi and Daniel T. Wallace | |

It is certified that error appears in the above-identified patent and that said Letters Patent is hereby corrected as shown below:

Title Page;

On the Face Sheet under (56) U.S. Patent Documents:

Please replace "4,843,939" with the following:

--4,943,939--

Signed and Sealed this

Eleventh Day of November, 2008

JON W. DUDAS
*Director of the United States Patent and Trademark Office*